United States Patent [19]

Barrows

[11] Patent Number: 5,990,310

[45] Date of Patent: Nov. 23, 1999

[54] METHOD FOR PREPARING SUBSTITUTED TRIAZINES

[75] Inventor: Franklin H. Barrows, Waterbury, Conn.

[73] Assignee: Uniroyal Chemical Company, Inc., Middlebury, Conn.

[21] Appl. No.: 09/288,350

[22] Filed: Apr. 8, 1999

[51] Int. Cl.⁶ .................................................. C07D 251/54
[52] U.S. Cl. .............................................................. 544/197
[58] Field of Search ............................................. 544/197

[56] References Cited

U.S. PATENT DOCUMENTS

| 4,650,867 | 3/1987 | Ronco et al. | 544/197 |
| 4,794,135 | 12/1988 | Wheeler et al. | 544/197 |
| 4,972,010 | 11/1990 | Wheeler et al. | 544/197 |
| 5,047,530 | 9/1991 | Wheeler et al. | 544/197 |
| 5,120,844 | 6/1992 | Wheeler et al. | 544/197 |

FOREIGN PATENT DOCUMENTS

| 859221 | 1/1961 | United Kingdom . |
| 1 279351 | 6/1973 | United Kingdom . |

*Primary Examiner*—John M. Ford
*Attorney, Agent, or Firm*—Raymond D. Thompson

[57] ABSTRACT

A method for preparing substituted triazines includes reacting a phenylazoaniline with a cyanuric halide to produce a (phenylazo) phenylamino-1,3,5-triazine, which is then reduced to form an aminoanilino-1,3,5-triazine. The aminoanilino-1,3,5-triazine can be alkylated under reducing conditions to produce an N-alkyl-phenylenediamino-1,3,5-triazine such as 2,4,5-tris-[N-alkyl-p-phenylenediamino]-1,3,5-triazine, which is useful as an antiozonant in rubber and other polymer formulations.

20 Claims, No Drawings

METHOD FOR PREPARING SUBSTITUTED TRIAZINES

BACKGROUND OF THE INVENTION

1. Field of the Invention

This invention relates to a process for the preparation of substituted triazines and derivatives thereof.

2. Background of the Related Art

Substituted triazines are commercially important compounds which find many uses in the chemical industry both as end products and intermediates. For example, 2,4,6-tris-[aminoanilino]-triazine is useful for synthesizing textile, leather and paper dyes as well as pigments. U.S. Pat. No. 4,650,867 discloses a method for preparing 2,4,6-tris-(aminophenylamino)-triazine by condensing s-chlorotriazine with a partially protected phenylenediamine and subsequently removing the protective groups.

Other substituted triazine have been found to be useful as antiozonants. It is well known that ozone causes surface cracking of conventional highly unsaturated rubber vulcanizates when the rubber is placed under strain in an ozone environment. The most severe deterioration occurs when a small number of cracks are formed which grow rapidly into deep, disruptive fissures. These ozone cracks seriously shorten the serviceable life of the article.

Chemical antiozonants have been developed which retard the formation of the ozone cracks occurring under static and dynamic conditions. Examples of antiozonants in common use include: N-phenyl-N'-(1-,3-dimethyl butyl)-p-phenylenediamine; N-phenyl-N'-isopropyl-p-phenylenediamine; N-phenyl-N'-(1,4-dimethylpentyl)-p-phenylenediamine; N-phenyl-N'-(1-methylheptyl)-p-phenylenediamine; N-phenyl-N'-cyclohexyl-p-phenylenediamine; mixed diaryl-p-phenylenediamines; N,N'-diphenyl-p-phenylenediamine; N,N'-di-beta-naphthyl-p-phenylenediamine; N,N'-bis-(1,4-dimethylpentyl)-p-phenylenediamine; N,N'-bis-(1-ethyl-3-methylpentyl)-p-phenylenediamine; N,N'-bis-(1-methylheptyl)-p-phenylenediamine; N-phenyl-N'-p-toluenesulfonyl-p-phenylenediamine, and blends of these materials.

The use of these well known paraphenylenediamine materials has improved ozone protection under both static and dynamic conditions, however, even the best of the class just described have a very strong tendency to both stain and discolor. The term "stain" or "staining" is herein used to describe the characteristic of a material to diffuse through a polymeric substrate and discolor the adjacent surface. This diffusion staining is highly objectionable in most light colored rubber articles. In tires, which is the largest application in which the ozone protection is required, the tendency to diffusion staining of the aforementioned paraphenylenediamine materials is objectionable particularly in white sidewall type tires. Even in non-white sidewall type tires, the tendency of the materials to diffuse to the surface of the tire sidewall can be objectionable in that a brown, dull surface is created on the tire sidewall. This is aesthetically objectionable in that it detracts from the general jet black, smooth appearance of a new tire. It is obvious that in a white sidewall tire, the migration of the brown discoloring material to the surface of the white sidewall is highly objectionable and generally difficult to remove during cleaning of the tire surface.

Waxes have been long utilized to inhibit ozone cracking in articles under stress in static condition by incorporating the wax into the rubber compound prior to vulcanization. The wax functions by migrating to the surface of the rubber article to form a film which acts as a physical barrier to the ozone attack. However, during dynamic flexing in service, the wax film is cracked or disrupted and the tendency is for the article to exhibit fewer and more severe ozone cracks than if no wax had been incorporated. Therefore, for many service conditions, the use of wax is impractical due to the dynamic conditions under which the article is expected to perform.

U.S. Pat. Nos. 5,120,844, 5,047,530, 4,972,010 and 4,794,135 disclose substituted 1,3,5-triazine compounds having at least one N-alkyl-p-phenylenediamino group on the triazine ring, which are useful as non-staining, long term antiozonants for unsaturated polymers. These compounds can be prepared by reacting N-alkyl phenylenediamine with a cyanuric halide. However, what is needed is a more economical and effective method of preparation.

SUMMARY OF THE INVENTION

A method is provided herein for preparing a substituted triazine which comprises:

a) reacting a phenylazoaniline with a cyanuric halide to produce a (phenylazo)phenylamino-1,3,5-triazine; and b) reducing the (phenylazo)phenylamino-1,3,5-triazine with a reducing agent to produce an aminoanilino-1,3,5-triazine.

The method advantageously provides a more cost efficient procedure for preparing an intermediate compound, which is useful for the synthesis of various end products, particularly antiozonants, and most particularly N-alkyl-p-phenylenediamino-1,3,5,-triazine, as described herein.

DETAILED DESCRIPTION OF THE INVENTION

The aminoanilino triazines which can be prepared according to the method of the present invention have the structure shown below as molecular formula (I):

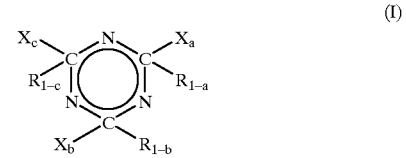

(I)

wherein X is a halogen selected from Cl, F, B, or I; a, b, and c are individually selected from either 0 or 1; and R is an aminoanilino group having the structure:

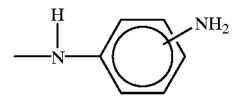

such that the amino groups are either in ortho, meta or para positions with respect to each other. The benzene ring of the aminoanilino group can be substituted with halogen (Cl, F, Br, I), hydroxy, nitro, or a lower alkyl group having from about 1 to about 5 carbon atoms. The para position is preferred so as to define a 4-aminoanilino group. The preferred values for a,b and c are 0, so as to define a 2,4,6-tris-[4-aminoanilino]-1,3,5-triazine structure as follows:

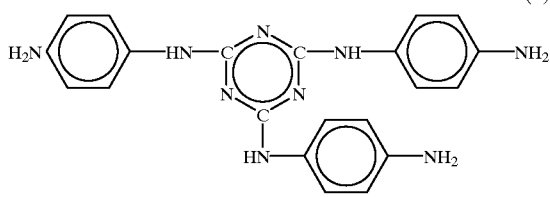

(II)

The substituted triazine of formula (I) is made in accordance with the following procedure:

In a first step a phenylazoaniline (i.e., an aminoazobenzene) is reacted with a cyanuric halide to produce a [(phenylazo)phenylamino]-triazine. The phenylazoaniline can be 3- or 4- phenylazolaniline. However, since the para position for the relative position of amino groups is preferred, the procedure will hereafter be exemplified with 4-phenylazoaniline (formula III) as the starting material:

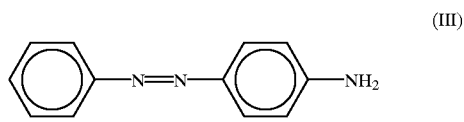

(III)

The benzene rings of the 4-phenylazoaniline can optionally have substituents such as halo (Cl, F, Br, I), nitro, hydroxy, or lower alkyl group. The cyanuric halide can be cyanuric chloride, fluoride, bromide, or iodide. Since chloride is preferred, the procedure will hereafter be exemplified with cyanuric chloride having formula (IV):

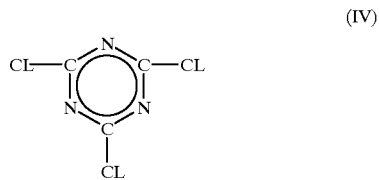

(IV)

The 4-phenylazoaniline can be prepared by methods commonly known in the art. The molar proportion of 4-phenylazoaniline to cyanuric chloride can be varied in accordance with the degree of substitution desired on the triazine ring. The 4-phenyazoaniline is preferably dissolved in a solvent (e.g., toluene, benzene or xylene) to which cyanuric chloride is added with stirring. The temperature is preferably about 25° C. at the start. The mixture is gradually heated to a temperature of from about 90° C. to about 120° C. and held at that temperature for several hours, while triethylamine (or other bases) and additional 4-phenylazoaniline are added. The reaction can be monitored by chromatographic techniques to determine the degree of conversion to the tri substituted 4-(phenylazo) phenylamino-1,3,5-triazine. This compound can be filtered out and washed with toluene and with water, then dried.

In a second step, the 2,4,6-tris-[4-(phenylazo) phenylamino]-1,3,5-triazine obtained from the first step is reduced by a reducing agent to form 2,4,6-tris-[aminoanilino]-1,3,5-triazine. The reduction is preferably performed in the presence of a catalyst.

The catalyst is preferably a metal of Group VIII of the Periodic Table of the Elements (CAS version), and more preferably, a noble metal such as platinum or palladium on a particulate support (e.g., carbon, alumina, silica, aluminosilicates, and the like).

The preferred reducing agent can be selected from, for example, hydrazine hydrate, and hydrogen.

The reduction can be performed by dissolving the 2,4,6-tris-[4-phenylazo)phenylamino]-1,3,5-triazine in a solvent such as isobutanol, and adding thereto the catalyst and the reducing agent. Hydrazine hydrate can be added directly to the solution at atmospheric pressure, or the solution can be sealed under pressure (about 100–1,000 psi, preferably about 200–800 psi, more preferably bout 400–700 psi) with hydrogen, while heating to a temperature of from 50° C. to about 110° C., more preferably 70° C. to about 100° C.

The reactor in which the reduction reaction is performed is held at reaction conditions for a period of time sufficient to achieve desired conversion while the reaction is periodically monitored by, e.g., liquid chromatography. Generally, the reaction is conducted for 5 to 15 hours.

The resulting 2,4,6-tris-[4-aminoanilino]-1,3,5-triazine is separated out by filtration and recovered. This compound can be used as an intermediate for various other chemicals or as an end product.

Optionally, the 2,4,6-tris-[4-aminoanilino]-1,3,5-triazine can be used to synthesize N-alkyl-p-phenylene diamino-1,3,5-triazines, which are useful as antiozonants, as mentioned above. The tris substituted compound is preferred.

Thus, the 2,4,6,-tris-[4-aminoanilino]-1,3,5-triazine can be reacted with an alkylating agent in a reductive alkylation reaction, preferably in the presence of a catalyst (e.g., Pt or Pd on carbon, alumina, silica or other support) under a hydrogen atmosphere at from about 200–1500 psi (preferably 500–1200 psi, more preferable 600–1000 psi), and a temperature of from about 100° C. to about 200° C. (preferably 150° C. to 190° C., more preferably 160° C. to about 180° C). The alkylating agent can be, for example, a ketone or an aldehyde having from about 3 to about 20 carbon atoms, more preferably from about 5 to about 15 carbon atoms, and most preferably from about 6 to about 10 carbon atoms. The alkylating agent can be a saturated straight chain, branched chain or cycloalkyl structure. The reaction is conducted for a period of time sufficient to obtain the desired degree of alkylation.

The 2,4,6-tris-[N-alkyl-p-phenylenediamino]-1,3,5-triazines prepared in accordance with the method described herein are characterized by the formula (V):

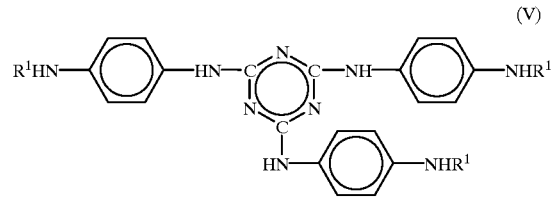

(V)

wherein $R^1$ is an alkyl group selected from straight, chain, branched or cycloalkyl saturated structures having from about 3 to 20 carbon atoms, preferably about 6 to about 10 carbon atoms.

The following examples are provided to illustrate the present invention:

EXAMPLE I

2,4,6-Tris-[4-(phenylazo)phenylamino]-1,3,5-triazine

In a two-liter, five-necked, round-bottom flask equipped with a thermocouple, a condenser, a mechanical stirrer, an addition funnel, and a nitrogen sweep were placed 40 grams (0.2 mole) of 98 percent 4-phenyl-azoaniline and 500 grams of toluene. Finely ground 99 percent cyanuric chloride (0.05 mole, 9.3 parts) was added with good stirring at 25° C. Over a period of one hour the reaction mixture was heated to 110° C., and held an additional seven hours at 110° C. During the hold time, triethylamine (0.15 mole, 15.3 parts) was gradually added, and an additional 20 grams (0.1 mole) of 4-phenylazoaniline was added. The reaction was followed by high performance liquid chromatography by observing the disappearance of the starting cyanuric chloride and the conversion of the intermediate, dichloro, and monochloro-triazines to the trisubstituted compound. The title compound was isolated by filtration at 90° C. The filter cake was washed with 300 milliliters of 80° C. toluene, then with 300 milliners of 80 C. water to remove triethylamine hydrochloride, dried to a constant weight to give 78.7 percent yield (26.2 grams) of 2,4,6-tris[4-phenylazo)phenylamino]-1,3,5-triazine. The melt point was 254°–257° C. The infrared spectrum was consistent with the structure. Relative HPLC analysis of the product showed it to be 95.8 percent pure.

EXAMPLE II 2,4,6-Tris-[4-(phenylazo)phenylamino]-1,3,5-triazine

The toluene filtrate from Example I was extracted with 250 milliters of water at 90° C., then placed in the apparatus used in Example I. Ninety (90) parts (0.45 mole) of 98 percent 4-phenylazoaniline and 18.5 parts (0.1 mole) of cyanuric chloride were added. Over a period of 1.5 hours, the reaction mixture was heated to 110° C. and held at 110° C. for an additional three hours with the gradual addition of 30.6 parts (0.3 mole) of triethylamine. The title compound was isolated at 90° C. by filtration, washed with 300 milliliters of 80° C. toluene and 300 milliliters of 80° C. water. The yield was 83.5 percent (55.6 grams), and the HPLC relative area analysis showed it to be 97.1 percent pure.

EXAMPLE III 2,4,6-Tris-[4-(phenylazo)phenylamino)-1,3,5-triazine

The toluene filtrate from Example II, 120 parts (0.6 mole) of 98 percent 4-phenylazoaniline, 27.8 parts (0.15 mole) of cyanuric chloride, 45.9 parts (0.45 mole) of triethylamine were used to produce 100.9 parts (101 percent yield of the title compound by following the procedure of Example II. The HPLC area percent assay was 96.9 percent.

EXAMPLE IV 2,4,6-Tris-[4-(phenylazo)phenylamino]-1,3,5-triazine

The toluene filtrate from Example III was extracted at 90° C. with 250 milliliters of water, then placed in the apparatus used in Example I. Then 300 milliners of toluene was distilled off, and 90 parts (0.45 mole) of 98 percent 4-phenylazoaniline, 27.8 parts (0.15 mole) of cyanuric chloride, 45.9 parts (0.45 mole) of triethylamine were used to produce 95.1 parts (95.2) percent yield) of the title compound by following the procedure of Example II. The HPLC are percent assay was 95.7 percent. The overall yield for the four reactions based on cyanuric chloride was 92.7 percent.

EXAMPLE V 2,4,6-Tris-[4-(phenylazo)phenylamino]-1,3,5-triazine

This example illustrates alcohols which can be used to prepare the title compound.

In a two-liter, four-neck, round-bottom flask equipped with a thermocouple, a mechanical stirrer, a condenser, and a nitrogen sweep were placed 80 grams (0.4 mole) of 98 percent 4-phenylazoaniline and 500 milliliters of isopropanol. The temperature was adjusted to 10° C., and 9.3 grams (0.5 mole) of finely ground cyanuric chloride was added. Over a period of one hour the reaction mixture was heated to 80° C., and held an additional four hours at 80° C. During the hold time, 6 grams (0.15 mole) of finely ground sodium hydroxide was added. An additional 500 milliliters of isopropanol was added, and the title compound was isolated by filtration at 70° C. The filter cake was washed with 250 milliliters of 70° C. isopropanol, then with warm water to remove the sodium chloride, dried to a constant weight to give 87.9 percent yield (29.2 grams) of 2,4,6-tris-[4-(phenylazo)phenylamino]-1,3,5-triazine. Relative area HPLC analysis showed it to be 91.4 percent pure. Using the above procedure, the isopropanol portion of the filtrate was recycled four times. The results are shown in Table 1:

TABLE I

| Recycle Run | Grams of Cyanuric Chloride | Grams of 4-Phenylazo-aniline | Grams of Sodium Bicarbonate | Yield, Grams | Yield % | Relative Area, % Assay |
|---|---|---|---|---|---|---|
| 1 | 9.3 | 30.2 | 12.6 | 35.6 | 106.9 | 93.9 |
| 2 | 9.3 | 30.2 | 12.6 | 33.3 | 100.0 | 93.5 |
| 3 | 9.3 | 30.2 | 12.6 | 30.8 | 92.5 | 91.3 |
| 4 | 9.3 | 30.2 | 12.6 | 32.9 | 98.8 | 93.0 |

The average yield based on cyanuric chloride was 97.2 percent with an average purity of 92.6 percent.

EXAMPLE VI 2,4,6-Tris-[4-aminoanilino]-1,3,5-triazine

In one 100 milliliter, four-neck, round-bottom flask equipped with a thermo-couple, a condenser, a mechanical stirrer, and a nitrogen sweep were placed 3.34 grams (0.005 mole) of 2,4,6-tris-[4-(phenylazo)phenylamino]-1,3,5-triazine, 50 grams of isobutanol, 1.66 grams (0.033 mole) of hydrazine hydrate and 0.15 gram of 5 percent palladium on carbon (approximately 60 percent wet). Over a period of two hours, the mixture was heated to 70° C., and held an additional ten hours at 70° C. The reduction was followed by high performance liquid chromatography by observing the disappearance of the starting tris-azo compound and the conversion of the intermediate di- and mono-azo compounds to the tris-amino compound and the formation of the by-product aniline. The title compound was isolated by filtration at 60° C. The filter cake was washed with 10 milliliters of isobutanol, dried to a constant weight to give 100 percent yield (2 grams) of 2,4,6-tris-[4-aminoanilino]-1,3,5-triazine. The melt point was 297°–299° C. The infrared spectrum was consistent with the structure. Relative area HPLC analysis showed it to be 97.8 percent pure. The filtrate was distilled to recover 1.1 grams of aniline, 78.6 percent of theory.

EXAMPLE VII 2,4,6-Tris-[4-aminoanilino]-1,3,5-triazine

A one-liter autoclave was charged with 18.7 grams (0.0281 mole) of 2,4,6-tris[4-(phenylamino]1,3,5 triazine, 198.2 grams of isobutanol and 4 grams of 5 percent Pd/C,50 percent wet catalyst. The autoclave was sealed and pressure checked, purged two times with nitrogen, one time with hydrogen, and pressured to about 600 psi with hydrogen. The contents of the autoclave were heated to 100° C., and held for three hours at 100° C. while maintaining the hydrogen pressure between 601–651 psi. The hydrogen take up was 96 percent of theory. The product was isolated by filtration, and weighed 11.1 grams (99.1 percent of theory), and the HPLC relative area analysis of the product showed to be 82.2 percent pure.

EXAMPLE VIII 2,4,6-Tris-[N-1,4-dimethylpentyl-p-phenylenediamino]-1,3,5-triazine A one-liter autoclave was charged with 50 grams (0.125 mole) of 2,4,5-tris-[4-aminoanilino]-1,3,5-triazine, 250 grams (2.19 moles) of 5-methyl-2-hexanone, and 4.78 grams (dry weight) of 3 percent Pd/C catalyst. The autoclave was sealed and pressure checked, purged two times with nitrogen, two times with hydrogen, and pressured to about 900 psi with hydrogen. The contents of the autoclave were heated to 165° C., and held for 3.5 hours at 164° C. while maintaining the hydrogen pressure between 604–904 psi. The hydrogen take up was 94 percent of theory. The catalyst was removed by filtration with the aid of Celite. The excess methyl isoamyl ketone was removed by vacuum distillation. The residue was 76 grams (87.6 percent of theory), and the HPLC assay was 84.4 percent.

What is claimed is:

1. A method for preparing a substituted triazine, comprising:
   a) reacting a phenylazoaniline with a cyanuric halide to produce a (phenylazo)phenylamino-1,3,5-triazine; and
   b) reducing the (phenylazo)phenylamino-1,3,5-triazine with a reducing agent to produce an aminoanilino-1,3,5-triazine having the formula:

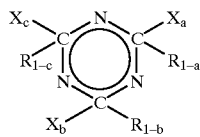

wherein X is a halogen selected from the group consisting of Cl, F, Br and I, a, b, and c are individually selected from 0 or 1, and R is an aminoanilino moiety having the structure

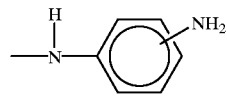

such that the amino groups of the aminoanilino moiety are in ortho, meta or para positions relative to each other.

2. The method of claim 1 wherein the benzene ring of the aminoanilino moiety includes one or more substituents selected from the group consisting of halogen, hydroxy, nitro and lower alkyl groups.

3. The method of claim 1 wherein the cyanuric halide is cyanuric chloride.

4. The method of claim 1 wherein the (phenylazo)phenylamino-1,3,5-triazine is 2,4,6-tris-[4-(phenylazo)phenylamino]-1,3,5-triazine.

5. The method of claim 1 wherein the aminoanilino-1,3,5-triazine is 2,4,6-tris-[4-aminoanilino]-1,3,5-triazine.

6. The method of claim 1 wherein step (a) is performed in a solvent.

7. The method of claim 6 wherein the solvent is selected from the group consisting of toluene, benzene and xylene.

8. The method of claim 6 wherein step (b) is performed in the presence of a catalyst.

9. The method of claim 8 wherein the catalyst comprises a Group VIII metal on a particulate support.

10. The method of claim 9 wherein the Group VIII metal is selected from the group consisting of platinum and palladium, and the particulate support is selected from the group consisting of carbon, alumina, silica, and aluminosilicates.

11. The method of claim 1 wherein the reducing agent is hydrazine hydrate.

12. The method of claim 1 wherein the reducing agent is hydrogen.

13. The method of claim 12 wherein step(b) is performed under a pressure of from about 100 to about 1,000 psi and at a temperature of from about 50° C. to about 110° C.

14. The method of claim 1 further including the step:
   c) alkylating the aminoanilino-1,3,5-triazine of step (b) with an alkylating agent under reducing conditions to form an N-alkyl-phenylenediamino-1,3,5-triazine.

15. The method of claim 14 wherein the aminoanilino-1,3,5-triazine is 2,4,6-tris-[4-aminoanilino]-1,3,5-triazine and the N-alkyl-phenylenediamino-1,3,5-triazine is 2,4,6-tris-[N-alkyl-p-phenylenediamino]-1,3,5-triazine having the formula:

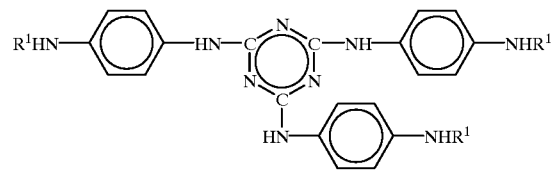

wherein $R^1$ is an alkyl moiety selected from the group consisting of saturated straight chain, branched chain and cycloalkyl moieties, the alkyl moiety having from about 3 to about 20 carbon atoms.

16. The method of claim 14 wherein the alkylating agent is a ketone having from about 3 to about 20 carbon atoms.

17. The method of claim 16 wherein the ketone is 5-methyl-2-hexanone.

18. The method of claim 14 wherein step (c) is performed in the presence of a catalyst.

19. The method of claim 18 wherein the catalyst comprises a noble metal selected from the group consisting of platinum and palladium, on a particulate support selected from the group consisting of a carbon, alumina, silica, and aluminosilicates.

20. The method of claim 14 wherein the reducing conditions include a hydrogen atmosphere, a pressure of from about 200 to about 1500 psi, and a temperature of from about 100° C. to about 200° C.

* * * * *